United States Patent
Zhao et al.

(10) Patent No.: US 9,707,262 B2
(45) Date of Patent: Jul. 18, 2017

(54) COMPOSITION WITH ANOXIA-TOLERANT AND ANTI-FATIGUE EFFECTS AND USE THEREOF

(71) Applicant: Infinitus (China) Company Ltd., Jiangmen (CN)

(72) Inventors: Hongwei Zhao, Guangzhou (CN); Shiyu Zou, Guangzhou (CN); Chungwah Ma, Guangzhou (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 0 days.

(21) Appl. No.: 14/715,619

(22) Filed: May 19, 2015

(65) Prior Publication Data
US 2016/0199431 A1 Jul. 14, 2016

(30) Foreign Application Priority Data
Jan. 8, 2015 (CN) .......................... 2015 1 0011658

(51) Int. Cl.
| | |
|---|---|
| A61K 36/815 | (2006.01) |
| A61K 35/32 | (2015.01) |
| A61K 36/52 | (2006.01) |
| A61K 36/54 | (2006.01) |
| A61K 36/64 | (2006.01) |
| A61K 36/725 | (2006.01) |
| A61K 36/77 | (2006.01) |
| A61K 36/79 | (2006.01) |
| A23L 33/105 | (2016.01) |
| A23P 10/30 | (2016.01) |

(52) U.S. Cl.
CPC .......... *A61K 36/815* (2013.01); *A23L 33/105* (2016.08); *A23P 10/30* (2016.08); *A61K 35/32* (2013.01); *A61K 36/52* (2013.01); *A61K 36/54* (2013.01); *A61K 36/64* (2013.01); *A61K 36/725* (2013.01); *A61K 36/77* (2013.01); *A61K 36/79* (2013.01); *A23V 2002/00* (2013.01)

(58) Field of Classification Search
None
See application file for complete search history.

(56) References Cited

PUBLICATIONS

Thomson Reuters abstract for Ban (CN 103555536 A, published Feb. 5, 2014), printed 2016.*
Thomson Reuters abstract for Zhao (CN 101748030 A, published Jun. 23, 2010), printed 2016.*
Chinese Herbs Healing "Jujube Fruit," online entry printed 2016; http://www.chineseherbshealing.com/jujube-fruit-da-zao/.*
Chinese Herbs Healing "Goji Berry," online entry printed 2016; http://www.chineseherbshealing.com/goji-berry/.*
Chinese Herbs Healing "Schizandra Berry," online entry printed 2016; http://www.chineseherbshealing.com/schizandra-berry/.*
Chinese Herbs Healing "Juglans Regia," online entry printed 2016; http://www.chineseherbshealing.com/juglans-regia-walnut/.*
dictionary.com "ratio," printed 2017; http://www.dictionary.com/browse/ratio.*
yingyanghouse.com "Jin Kui Shen Qi Wan," printed 2017; https://store.yinyanghouse.com/shop/chinese-herbal-medicine/jin-kui-shen-qi-wan.*
PTAB Affirmance of product of nature rejection under 35 USC 101 in U.S. Appl. No. 13/748,964 (Appeal 2015-000614), mailed Feb. 14, 2017.*

* cited by examiner

*Primary Examiner* — David J Blanchard
*Assistant Examiner* — Alissa Prosser
(74) *Attorney, Agent, or Firm* — Yue Xu; U.S. Fairsky LLP

(57) ABSTRACT

A composition with anoxia-tolerant and anti-fatigue functions, which is prepared by the following active ingredients: Arillus Longan, Fructus Jujubae, Radix Rehmanniae Preparata, Fructus Lycii, Semen Juglandis, Fructus Schisandrae Chinensis, Cortex Cinnamomi, and Cornu Cervi Pantotrichum. The invention further provides a use of aforesaid composition in the preparation of the health food with anoxia-tolerant and anti-fatigue functions. The health food of the present invention is prepared with natural Chinese herbal medicine as the major raw materials, can be administered for a long time, the result of functional experiment prove that, the health food of the present invention has anoxia-tolerant and anti-fatigue functions, the effect is significant.

8 Claims, No Drawings

COMPOSITION WITH ANOXIA-TOLERANT AND ANTI-FATIGUE EFFECTS AND USE THEREOF

CROSS-REFERENCE TO RELATED APPLICATIONS

This application claims priority from CN Application No. 201510011658.7, filed Jan. 8, 2015, the contents of which are incorporated herein in the entirety by reference.

FIELD OF THE INVENTION

This invention relates to the field of food and dietary supplements, and particularly relates to a composition with anoxia-tolerant and anti-fatigue functions prepared from natural Chinese herbal medicine as the main raw material, and use thereof.

BACKGROUND OF THE INVENTION

Increased competition and accelerated rhythm in the modern society make people live in an stressful environment, under a high work pressure and stress for long periods of time, which are usually accompanied by the following symptoms in terms of Traditional Chinese Medicine (TCM hereinafter), such as "limbs chill," "limp aching lumbus and knees", premature graying or losing hairs at a early stage, nocturia, sexual function decline, suppressed immune function and "kidney vacuity". According the TCM theory, kidney vacuity (or the kidney function weakened) is mainly caused by "three overexertions": "physical overexertion", "mind fatigue" and "sexual overindulgence". Fatigue, high strength in the work, always work overtime and late at night will cause the body into a continuous state of fatigue, causing symptoms of kidney vacuity; secondly, high work pressure and living pressure cause the body unable to relax, thus inducing kidney vacuity; thirdly, too frequent and overindulged sexual activity result in "Essence" and "Qi" incompetent, thus causing symptoms of kidney vacuity.

Therefore, how to delay the onset of fatigue, eliminate fatigue rapidly, restore energy and maintain a strong energy is extremely important, it becomes one of the hot issues of social concern. In the prior art, the products alleviating fatigue by supplementing Kidney are mostly traditional Chinese medicines, such as Jingui Shenqi Pill, Liuwei Dihuang Pill, Qiyuan Guihua extract, Shenling Baizhu San, etc. Clinical research works for improving kidney vacuity-caused fatigue of traditional vacuity-by using Chinese medicinal materials such as Herba Epimedii, Cornu Cervi Pantotrichum, Radix Morindae Officinalis, Radix Panacis Quinquefolii (American ginseng), Herba Rhodiolae, Radix Astragali seu Hedysari, Radix Angelicae Sinensis, Rhizoma Polygonati, etc. were also reported, but these products can not be used for a long time, due to their side effects.

SUMMARY OF THE INVENTION

The purpose of the present invention is to provide a composition with anoxia-tolerant and anti-fatigue effects, the active ingredients of the composition are prepared with various natural Chinese herbal medicine as the raw materials. The prepared composition, with a kidney-supplementing, anoxia-tolerant and anti-fatigue functionalities, can be administered for an extended time without side effect.

The purpose of the present invention is to further provide the use of aforesaid composition in the preparation of the health food with anoxia-tolerant and anti-fatigue functions.

The first purpose of the present invention is achieved by the following technical solution: a composition with anoxia-tolerant and anti-fatigue functions, the composition is prepared by the active ingredients: Arillus Longan, Fructus Jujubae, Radix Rehmanniae Preparata, Fructus Lycii, Semen Juglandis, Fructus Schisandrae Chinensis, Cortex Cinnamomi, and Cornu Cervi Pantotrichum.

As a preferable technical solution of the present invention, the composition of the present invention with anoxia-tolerant and anti-fatigue functions, wherein the ratio by weight of individual active ingredient is: Arillus Longan 10-150, Fructus Jujubae 10-150, Radix Rehmanniae Preparata 10-150, Fructus Lycii 10-150, Semen Juglandis 10-150, Fructus Schisandrae Chinensis 3-50, Cortex Cinnamomi 3-50, Cornu Cervi Pantotrichum 3-50.

The ratio by weight of individual active ingredient is further preferably: Arillus Longan 20-90, Fructus Jujubae 20-90, Radix Rehmanniae Preparata 20-90, Fructus Lycii 20-90, Semen Juglandis 15-90, Fructus Schisandrae Chinensis 5-20, Cortex Cinnamomi 3-20, Cornu Cervi Pantotrichum 3-20.

The ratio by weight of individual active ingredient is optimally: Arillus Longan 25, Fructus Jujubae 25, Radix Rehmanniae Preparata 20, Fructus Lycii 20, Semen Juglandis 15, Fructus Schisandrae Chinensis 8, Cortex Cinnamomi 5, Cornu Cervi Pantotrichum 5.

The individual active ingredient in the composition with anoxia-tolerant and anti-fatigue functions of the present invention, has the following efficacy and characters:

Arillus Longan is initially recorded in the "Shen Nong's Herbal Classic", it has been regarded as a precious tonic since ancient times, and has more than a thousand years of history as a tonic medicine and health food, it has the effects of supplementing Heart and boosting Spleen, nourishing Blood and soothing Essence. It is recorded in several editions of "Chinese Pharmacopoeia". It is commonly clinically used for insufficiency of Qi and Blood, palpitation and fearful throbbing, forgetfulness and insomnia, Blood deficiency and chlorosis. Modern medical research also shows that, Arillus Longan has obvious effects of anti-oxidation, anti-aging, enhancing immunity etc.

Fructus Jujubae has a long edible history, has been illustrated in "Treatise on Cold-induced Febrile Diseases", "Synopsis of Golden Chamber" and "Compendium of Materia Medica" a lot. It is a commonly used in Traditional Chinese Medicine (TCM) for supplementing the Center and boosting Qi, nourishing Blood for tranquillization, moderates the nature of medicines. Modern nutritional studies show that, Fructus Jujubae not only contains protein, sugars, organic acids, fats, and 18 kinds of amino acids essential to human body, as well as iron, zinc, phosphorus, calcium, selenium, etc., but also is rich in vitamins A, B2, C and various biological active ingredients. Fructus Jujubae polysaccharide is an important active substance in the Fructus Jujubae, which has an obvious complement activity and promoting the proliferation of lymphocyte, can improve organism immunity. The fructose, oligosaccharides, acidic polysaccharides in Fructus Jujubae participate in hepatoprotection, Fructus Jujubae polysaccharide can alleviate the symptoms of carbon tetrachloride-induced liver injury, and accelerate the regeneration speed of hepatic cells. In the mean time, Fructus Jujubae can improve the in vivo monocyte phagocytic function, has the roles of protecting liver, enhancing physical strength.

Radix Rehmanniae Preparata is initially recorded in "Illustrated Classics of Materia Medica", it has sweet flavor, slightly warm nature, meridian tropism in liver and kidney. It has efficacies of Blood-supplementing and Yin-enriching, Essence-boosting and marrow-replenishing, has regulatory role on the endocrine system, cardiovascular system, immune system etc., in which the crude polysaccharide of Radix Rehmanniae Preparata is the major component of Radix Rehmanniae Preparata for promoting hematopoietic and immune functions, the crude polysaccharide of Radix Rehmanniae Preparata can significantly improve the hematopoietic function of model mice, while having a rather good improvement and stimulation effects on the immune system. It can significantly promote the activities of blood superoxide dismutase (SOD), catalase (CAT) and glutathione (GSH-PX), reduce the lipid peroxide (LPO) level in the plasma, brain homogenate and liver homogenate, has a good antioxidant effect, as well as the effects of promoting hematopoietic, anti-fatigue, anti-aging, enhancing immunity, anti-mutagenic, and inhibiting tumor etc.

Fructus Lycii is a conventional precious traditional Chinese medicinal material in China, commonly has a reputation as "Ruby", it is rich in vegetable polysaccharides, proteins, vitamins etc. As early in the "Shen Nong's Herbal Classic", it is recorded that administration for a long time strengths sinew and bone; the "alternative recordings of doctors" recites that the Fructus Lycii is good at "nourishing and supplementing Essence and Qi"; "Materia Medica for Dietotherapy" also recorded that Fructus Lycii "can benefit people, deplete vacuity fatigue". The Efficacy of Fructus Lycii in the aspects of nourishing Liver and Kidney, boosting Essence and brightening the eyes are also recommended by ancient physicians and dietotherapist. The Fructus Lycii polysaccharide in the Fructus Lycii is an important active ingredient, research show that, Fructus Lycii polysaccharide is a major active ingredient of Fructus Lycii for regulating immunity and delaying aging, which also has positive effects on the prevention and treatment of malignant tumors and AIDS. In addition, it has the effects of relieving the symptoms of fatiguability, loss of appetite and poor vision, as well as lowering blood pressure, anti-fatty liver, anti-tumor, and anti-aging.

Semen Juglandis, as recorded in the "Compendium of Materia Medica", has the efficacies of supplementing Qi and nourishing the Blood, moistening Dryness and revolving Phlegm, and benefiting the Life gate, thus is considered to be a good material for supplementing Qi and nourishing the Blood, and nourishing the Brain and improving intelligence, as well as anti-aging. A lot of relevant experiments report that, Semen Juglandis has the effects of scavenging free radicals, anti-oxidation, anti-aging, supplementing Kidney and invigorating Yang. Semen Juglandis is extremely rich in fat, wherein the fatty acid is the fatty acid linoleic acid essential for human body, which is an important component of cell membrane, and has a good anti-oxidation function.

Fructus Schisandrae Chinensis is a traditional Chinese medicinal material having a long history of administration, as initially recorded in the "Shen Nong's Herbal Classic" as written in the Eastern Han Dynasty, it is ranked as a top material, and recorded as: This material supplements Qi, treats cough and counterflow Qi ascent, taxation damage and skinny thin, supplements the insufficiency, strengthens Yin, and benefits Jing of man. There is ancient records of its effects for nourishing the five organs, eliminating Heat, supplementing vacuity fatigue, making one looks bright, and brightening the eyes. Modern pharmacological studies have shown that Fructus Schisandrae Chinensis has activities such as promoting the stimulation of central nervous system, enhancing the Essence and Spirit of human body, physical strength and the tension of cardiovascular systems and systolic force, reducing serum glutamic-pyruvic transaminase (GPT) in viral hepatitis, thus having various aspects of beneficial effects to human body.

Cortex Cinnamomi has acrid, sweet and hot flavors, meridian tropism in kidney, spleen, heart and liver, it is a material for warming and supplementing Pure Yang, has efficacies of supplementing Fire and reinforcing Yang, dissipating Cold and relieving pain, warming the channels and freeing the vessels. It is widely used in clinical for the patients with Kidney Yang insufficiency, debilitation of Life gate fire, debilitation of spleen and kidney Yang and for treating the symptoms of cold pain in the stomach duct and abdomen. Modern pharmacological studies have shown that Cortex Cinnamomi have good effects on the diseases of digestive system, cardiovascular system and immune system, has analgesic, anti-bacterial and anti-tumor effects.

Ccornu Cervi Pantotrichum, being the non-ossified antler with dense hair from Sika deer, *Cervus elaphus* or buck, is a conventional precious traditional Chinese medicinal material, has a medicinal administration history of more than 2,000 years. Classical medical book "Shen Nong's Herbal Classic" records its functions and indications in details: "sweet taste, warm flavor, mainly treats metrostaxis and malign blood, Cold-Heat and fright epilepsy, supplements Qi and strengthens Zhi, makes teeth grow and prevents aging". In the "Compendium of Materia Medica" written by Li Shizhen in Ming dynasty, it records that, Ccornu Cervi Pantotrichum, engenders Essence and boosts marrow, nourishes Blood and benefits Yang, strengthens sinew and bone, cures all vacuities, deafness, dim vision, dizziness, vacuity dysentery". Modern medicine has proved that Cornu Cervi Pantotrichum contains a variety of bioactive substances, and has antioxidant and anti-aging effects, it has efficacies of improving sexual function, improving endurance, enhancing memory, enhancing immunity of body, and promoting protein synthesis in vivo.

TCM believes that the Kidney is the foundation of congenital constitution, governs bone, stores Essence, and engenders marrow. Water and Fire in the Kidney are the roots of Yin and Yang in human body, which ensure each living activity in human body to be performed normally. The strength of Kidney, directly relates to people's mental and physical strength. Kidney stores Essence, which is the source of Qi and Blood, thus affects the body's growth, development, reproduction and other life processes. The "Plain Questions•Far ancient Naïve Classis" (素问·上古天真论) illustrates in details that with the charge of Kidney Essence, human body grows and develops, becomes energetic and vigorous; with the consumption of Kidney Essence, the Qi, Blood, meridians, five organs and six bowels in human body debilitate, and therefore the "five Organs are debilitated, sinew and bones are resolved (五藏皆衰, 筋骨解堕)", and fatigue inevitable happens. The "Magic Pivot•Sea classic" also illustrates that the situation that fatigue occurs when the kidney essence is insufficient, and the sea of marrow fails to charge. It records that "insufficient sea of marrow, makes brain spin and ears ring, lower leg ache and veiling dizziness, loss of vision, slack thus lying". Kidney vacuity may cause fatigue, and fatigue is often an important feature of kidney vacuity. The "Plain Questions•Ping Ren Qixiang Classis (平人气象论)": "slow and stagnant cubit pulse, that is so called fatigue". According to the "category classic-Disease category": "Physical fatigue, that is so called intolerant of troubles and labors, looks sleepy and tired".

In the present invention, Cornu Cervi Pantotrichum is good at treating vacuity fatigue, beneficiary to Essence and Blood, and Conserving Spirit; Cortex Cinnamomi warms Yang and dissipates cold, supplements Fire to inspire the insufficient Yang Qi in Kidney, supplements the Fire in Life gate, and directs the Fire to the source; then assisted by Radix Rehmanniae Preparata, Fructus Lycii, Fructus Schisandrae Chinensis, for nourishing and supplementing Kidney Yin, promotes growing Yin fluid; Fructus Jujubae, Arillus Longan, Semen Juglandis supplements Kidney, nourishes Blood and tranquilizes, supplements both the Yin and Yang, which causes "Yang was assisted by Yin, and there is infinite growth and transformation". The combination of various medicines achieves the effect of warming and supplementing Kidney Yang.

The second purpose of the present invention is achieved by the following technical solution: the use of aforesaid composition in the preparation of the health food with anoxia-tolerant and anti-fatigue functions.

The aforesaid health food of the present invention with both anoxia-tolerant and anti-fatigue functions, can be prepared to be various pharmaceutically dosage forms by conventional processes (e.g., aqueous extraction or ethanol extraction), such as tablet, capsule, powder, granule, effervescent agent, drink, mixture or oral liquid.

The present invention has the following advantages:

(1) The composition of the present invention takes Cornu Cervi Pantotrichum as monarch drug, according to TCM complex theory, assisted by various conventional Chinese herbal medicines having anti-fatigue and anoxia-tolerant functions, such as Fructus Lycii, Radix Rehmanniae Preparata, upon overall conditioning, the composition plays the best health-care efficacy, it does not stick to the ancient prescription and is innovative;

(2) The health food of the present invention can be administered for a long time safely and effectively;

(3) The present invention prescribes under the instruction of TCM theory, with anoxia-tolerant survival duration at normal pressure of mice as the observing index, evaluates the effect of the health food of the present invention on the anoxia-tolerant ability of experimental animals at normal pressure; with the load swimming time of mice as the observing index, evaluates the antifatiguability of mice; together with the post-exercise blood lactate level of mice as the observing index, evaluates the aerobic metabolism and antifatiguability of mice, the results show that, the health food of the present invention can prolong the survival duration of mice at normal pressure under anoxia condition, and can improve the aerobic metabolism level and antifatigue effects in mice body;

(4) Upon research of functional experiments, the composition of the present invention is proved to have anoxia-tolerant and antifatigue effects.

The present invention will be further illustrated by the specific following embodiments and the results of functional studies.

DETAILED DESCRIPTION OF PARTICULAR EMBODIMENTS OF THE INVENTION

Part One The composition with anoxia-tolerant and anti-fatigue functions, health food and preparation process thereof Example 1

A composition with anoxia-tolerant and anti-fatigue functions provided by this Example, the composition is prepared by the following active ingredients:

Arillus Longan 100 g, Fructus Jujubae 150 g, Radix Rehmanniae Preparata 150 g, Fructus Lycii 100 g, Semen Juglandis 150 g, Fructus Schisandrae Chinensis 30 g, Cortex Cinnamomi 30 g, Cornu Cervi Pantotrichum 30 g are sampled.

The aforesaid raw materials are prepared to be tablet according to the following steps:

After the medicinal raw materials Arillus Longan, Fructus Jujubae, Radix Rehmanniae Preparata, Fructus Lycii, Semen Juglandis, Fructus Schisandrae Chinensis, Cortex Cinnamomi, Cornu Cervi Pantotrichum are concentrated upon boiling extraction, appropriate amount of purified water is added, tablet is prepared by conventional processes, the product can be administered as a health food.

Example 2

A composition with anoxia-tolerant and anti-fatigue functions provided by this Example, the composition is prepared by the following active ingredients:

Arillus Longan 150 g, Fructus Jujubae 100 g, Radix Rehmanniae Preparata 100 g, Fructus Lycii 150 g, Semen Juglandis 100 g, Fructus Schisandrae Chinensis 50 g, Cortex Cinnamomi 30 g, Cornu Cervi Pantotrichum 50 g are sampled.

The aforesaid raw materials are prepared to be capsule according to the following steps:

After Arillus Longan, Fructus Jujubae, Radix Rehmanniae Preparata, Fructus Lycii, Semen Juglandis, Fructus Schisandrae Chinensis, Cortex Cinnamomi, Cornu Cervi Pantotrichum are concentrated upon boiling extraction, spray-dried, the extracted dry powder of Chinese herbal medicine is obtained, the pre-gelatinized starch is added to the extracted dry powder of Chinese herbal medicine, mixed, granulated, dried, then magnesium stearate and talc powder are added, hard capsules are charged, the product can be administered as a health food.

Example 3

A composition with anoxia-tolerant and anti-fatigue functions provided by this Example, the composition is prepared by the following active ingredients:

Arillus Longan 250 g, Fructus Jujubae 250 g, Radix Rehmanniae Preparata 200 g, Fructus Lycii 200 g, Semen Juglandis 150 g, Fructus Schisandrae Chinensis 80 g, Cortex Cinnamomi 50 g, Cornu Cervi Pantotrichum 50 g are sampled.

The aforesaid raw materials are prepared to be oral liquid according to the following steps:

After Arillus Longan, Fructus Jujubae, Radix Rehmanniae Preparata, Fructus Lycii, Semen Juglandis, Fructus Schisandrae Chinensis, Cortex Cinnamomi, Cornu Cervi Pantotrichum are concentrated upon boiling extraction, appropriate amount of purified water is added, oral liquid is prepared by conventional processes, the product can be administered as a health food.

Example 4

A composition with anoxia-tolerant and anti-fatigue functions provided by this Example, the composition is prepared by the following active ingredients:

Arillus Longan 1200 g, Fructus Jujubae 1000 g, Radix Rehmanniae Preparata 1200 g, Fructus Lycii 1050 g, Semen Juglandis 1200 g, Fructus Schisandrae Chinensis 300 g, Cortex Cinnamomi 350 g, Cornu Cervi Pantotrichum 400 g are sampled.

The aforesaid raw materials are prepared to be capsule according to the following steps:

After Arillus Longan, Fructus Jujubae, Radix Rehmanniae Preparata, Fructus Lycii, Semen Juglandis, Fructus Schisandrae Chinensis, Cortex Cinnamomi, Cornu Cervi Pantotrichum are concentrated upon boiling extraction, spray-dried, the extracted dry powder of Chinese herbal medicine is obtained, the pre-gelatinized starch is added to the extracted dry powder of Chinese herbal medicine, mixed, granulated, dried, then magnesium stearate and talc powder are added, hard capsules are charged, the product can be administered as a health food.

Example 5

A composition with anoxia-tolerant and anti-fatigue functions provided by this Example, the composition is prepared by the following active ingredients:

Arillus Longan 1500 g, Fructus Jujubae 1500 g, Radix Rehmanniae Preparata 1500 g, Fructus Lycii 1500 g, Semen Juglandis 1000 g, Fructus Schisandrae Chinensis 500 g, Cortex Cinnamomi 500 g, Cornu Cervi Pantotrichum 500 g are sampled.

The aforesaid raw materials are prepared to be tablet according to the following steps:

After Arillus Longan, Fructus Jujubae, Radix Rehmanniae Preparata, Fructus Lycii, Semen Juglandis, Fructus Schisandrae Chinensis, Cortex Cinnamomi, Cornu Cervi Pantotrichum are concentrated upon boiling extraction, spray-dried, the extracted dry powder of Chinese herbal medicine is obtained. Microcrystalline cellulose, pre-gelatinized starch, and CMS-Na are added to the extracted dry powder of Chinese herbal medicine, mixed, granulated, dried, granule homogenized, magnesium stearate is added, pressed to obtain tablet, the product can be administered as a health food.

Example 6

A composition with anoxia-tolerant and anti-fatigue functions provided by this Example, the composition is prepared by the active ingredients in following ratios by weight: Arillus Longan 10, Fructus Jujubae 150, Radix Rehmanniae Preparata 10, Fructus Lycii 150, Semen Juglandis 10, Fructus Schisandrae Chinensis 50, Cortex Cinnamomi 3, Cornu Cervi Pantotrichum 50.

Example 7

A composition with anoxia-tolerant and anti-fatigue functions provided by this Example, the composition is prepared by the active ingredients in following ratios by weight: Arillus Longan 150, Fructus Jujubae 10, Radix Rehmanniae Preparata 150, Fructus Lycii 10, Semen Juglandis 150, Fructus Schisandrae Chinensis 3, Cortex Cinnamomi 50, Cornu Cervi Pantotrichum 3.

Example 8

A composition with anoxia-tolerant and anti-fatigue functions provided by this Example, the composition is prepared by the active ingredients in following ratios by weight: Arillus Longan 20, Fructus Jujubae 90, Radix Rehmanniae Preparata 20, Fructus Lycii 90, Semen Juglandis 15, Fructus Schisandrae Chinensis 20, Cortex Cinnamomi 3, Cornu Cervi Pantotrichum 20.

Example 9

A composition with anoxia-tolerant and anti-fatigue functions provided by this Example, the composition is prepared by the active ingredients in following ratios by weight: Arillus Longan 90, Fructus Jujubae 20, Radix Rehmanniae Preparata 90, Fructus Lycii 20, Semen Juglandis 90, Fructus Schisandrae Chinensis 5, Cortex Cinnamomi 20, Cornu Cervi Pantotrichum 3.

The aforesaid used medicinal raw materials and excipients are commercially available if not particularly specified. The composition in Examples 6-9 can be prepared to be various pharmaceutically dosage forms by conventional processes, such as oral liquid, capsule, tablet, powder, drink, mixture or granule etc., for use as a health food.

Part Two Functional Studies of the Health Food of the Present Invention 2.1 Animal Experiment for Anoxia-Tolerant Efficacy 2.1.1 Animal Grouping Each experiment was divided into four groups: blank control group (distilled water), high, medium and low-dosage experimental groups. 10 mice were randomly assigned to each group. The mice in each group were continuously intragastrically administrated for 30 d, no diet control during the experiment period. Body weight was weighed every 6 d, recorded, and the administration amount was adjusted according to body weight change.

2.1.2 Preparation of the Test Product

Equivalent dosage of mouse is equal to 10 folds of the human body recommended amount, 0.134 mL/per/day of the test product is the low dosage, 0.268 mL/per/day is the medium dosage, 0.402 mL/per/day is the high dosage. After a continuously intragastric administration of equal volume of the test product for 30 d, each index was measured.

2.1.3 Measurement Index

Except body weight change, the duration required by animal death were measured respectively in 3 different anoxia conditions being normal pressure, sodium nitrite poisoning, and acute cerebral ischemia (accurate to 0.1 second).

2.1.4 Experimental Methods 2.1.4.1 Normal-Pressure Anoxia-Tolerant Experiment

The mice in each group were continuously intragastrically administrated for 30 d, the blank control group was administrated with equal volume of solvent. 1 h after the last administration, the mice in each group were placed into the 250 mL ground-mouth bottles containing 5 g of soda lime (one per bottle), sealed the mouth with vaseline, to make it airtight, counted time immediately by stopwatch, with respiratory arrest as the observing index, observed the duration of mouse lived before anoxia-caused death.

2.1.4.2 Sodium Nitrite Poisoning Survival Experiment

The mice in each group were continuously intragastrically administrated for 30 d, the blank control group was administrated with equal volume of solvent. 1 h after the last administration, the mice in each group were intraperitoneally injected with sodium nitrite in a dosage of 200-240 mg/kg, counted time immediately after injection was finished, the survival duration after poisoning of mice were recorded.

2.1.4.3 Acute Cerebral Ischemia Anoxia Experiment

The mice in each group were continuously intragastrically administrated for 30 d, the blank control group was administrated with equal volume of solvent. 1 h after the last administration, the mice in each group were decollated from neck individually, counted time immediately, the length of time from decollation to open-mouth respiratory arrest were recorded.

2.1.5 Statistical Analysis

Data conversion and statistical analysis are performed using SPSS13.0 software. During the analysis, firstly, homogeneity of variance test is performed on the data, if there is homogeneity of variance, overall comparison is performed using ANOVA, if difference is found, pairwise comparisons are then performed by LSD method or Dunnett's method between the means of multiple dosage groups and control group. If there lacks heterogeneity of variance, then appropriate variable conversion is performed on the original data, statistics is performed on the converted data after satisfying the requirement of homogeneity of variance test, if the variable after conversion still can not satisfy the requirement of homogeneity of variance, changed to rank sum test to perform statistics, if difference is found when using overall comparison, pairwise comparisons are performed by the Tamhane's T2 test without requiring homogeneity of variance. As a result, groups are compared by mean and standard deviation (X±S).

2.1.6 Determination of Result

According to "Technical Standards for Testing & Assessment of Health Food (2003 edition)", the test sample is determined to have an anoxia-tolerant function according to the following standard.

Any two experimental results of normal-pressure anoxia-tolerant experiment, sodium nitrite poisoning survival experiment, and acute cerebral ischemia anoxia experiment have statistical significance.

2.1.6.1 Normal-pressure anoxia-tolerant experiment, results are as shown in the following Table 1: The mean of survival duration of mice in test groups is relatively higher than blank group, with the increase of concentration, the mean of survival duration of mice shows an increasing tendency, in particular the high dosage group increases more significantly than the blank control. It is known from variance analysis (homogeneity of variance) that, F constant=1.335, P constant=0.264, P>0.05, the difference between the duration required by death from anoxia in each group of mice is not significant, the reasons may be: (1) in condition that the administration duration are the same, the increase of the intragastric concentration in mice may improve the significance of result; (2) in condition that the setting of administration concentration are the same, extends intragastric duration (e.g., 45 d) appropriately, the difference between the survival duration of different dosage groups of mice may be significant, a clear dose-response relationship may be revealed.

TABLE 1

The duration required by anoxia-caused death of each group of mice

| | Sample number | Survival duration (X ± S) |
|---|---|---|
| blank group | 10 | 1509.9 ± 210.3 |
| low dosage group | 10 | 1604.6 ± 302.1 |
| medium dosage group | 10 | 1589.1 ± 365.2 |
| high dosage group | 10 | 1723.2 ± 297.6 |

2.1.6.2 Sodium nitrite poisoning survival experiment, results are as shown in the following Table 2: It is known from the comparison of three dosage (high, medium, low) groups of the oral liquid of the present invention and blank group that, the mean of gasping breathing duration of each experiment group of mice is higher than the blank group (P value 0.05), the survival duration of all the mice administered with three gradient concentrations of sample are significantly higher than the survival duration of blank group of mice, and from low dosage to high dosage, with the increase of administration concentration, the mean of gasping breathing duration also shows an increasing tendency, and shows a concentration-response correspondence. It is known from the result of variance analysis (homogeneity of variance) that, F sodium nitrite=2.588, P sodium nitrite=0.036<0.05 (=0.05), which demonstrates that the difference of test sample in the present experiment from the blank group in the aspect of improving survival duration of mice after sodium nitrite poisoning has statistical significance. The administration dosage and poisoning survival duration of experiment group of animals demonstrates a dosage-effect relationship, the survival duration of high dosage group increases significantly.

TABLE 2

The survival duration of each group of mice after sodium nitrite poisoning

| Grouping | Sample number | Survival duration (X ± S) | P value in comparison with blank group |
|---|---|---|---|
| blank group | 10 | 902.1 ± 164.4 | |
| low dosage group | 10 | 1182.2 ± 309.6 | 0.03 |
| medium dosage | 10 | 1219.9 ± 376.3 | 0.02 |
| high dosage group | 10 | 1302.9 ± 172.1 | <0.01 |

2.1.6.3 Acute cerebral ischemia anoxia experiment, results are as shown in the following Table 3: from the comparison of three dosage (high, medium, low) groups of the oral liquid of the present invention and blank group, the survival duration of acute cerebral ischemia anoxia each group of mice has statistical significance. The administration dosage and gasping duration of cerebral ischemia anoxia of experiment group of animals demonstrates a clear dosage-effect relationship, the high dosage group has a significant effect. It is known from the result of variance analysis (homogeneity of variance) that, F acute=17.743, P acute <0.01, which demonstrates that the acute cerebral ischemia anoxia experiment model as a whole has statistical significance, which demonstrates that the duration of each group of mice in the experiment from decollation to open-mouth respiratory arrest (hereinafter referred to as gasping duration) has significant difference. It demonstrates that the test sample is able to reduce the energy, oxygen consumption of brain, which may be related to increasing the sodium potassium adenosine triphosphatase activity. And from low dosage to high dosage, with the increase of administration concentration, the mean of gasping duration also shows an increasing tendency, and shows a concentration-response correspondence to a certain extent.

TABLE 3

The comparison of the duration of each experiment group from decollation to open-mouth respiratory arrest

| Grouping | Sample number | Survival duration (X ± S) | P value in comparison with blank group |
| --- | --- | --- | --- |
| blank group | 10 | 11.9 ± 2.3 | |
| low dosage group | 10 | 14.6 ± 1.4 | 0.01 |
| medium dosage※ | 10 | 14.4 ± 1.8 | 0.02 |
| high dosage group | 10 | 18.1 ± 1.9 | <0.01 |

To sum up, in condition of the present experiment lab, continuous orally intragastrically administrate with distilled water, and test sample respectively, each for 30 days, in three sub-experiments of the anoxia-tolerant experiment of the present health-care product, the gasping duration of each group in the sodium nitrite poisoning survival experiment and acute cerebral ischemia anoxia experiment has significant difference, showing a rather obvious dosage-effect relationship, and the effect of high dosage group is significant.

According to "Technical Standards for Testing & Assessment of Health Food (2003 edition)", the conclusion of animal experiment study is that the test sample has the effect of improving anoxia-tolerant function.

2.2 Result of Relieving Physical Fatigue Function Experiment

Western doctors think that fatigue is a physiological process of the body that can not maintain its function at a particular level and (or) can not maintain a predetermined exercise intensity. After movement, the body is in a hypoxic state, a large amount of materials causing fatigue are accumulated in the body, mainly lactic acid, blood ammonia and blood urea nitrogen (BUN). Short-term fatigue can be effectively alleviated after a rest, but if the fatigue is accumulated for a long time, it can not be eliminated, it will develop into redundant fatigue, which further leads to cerebral hypoxia and nervous system disorders, and is harmful to human health to some extent.

The most objective performance of fatigue is decline in sport endurance, and exhaustive swimming duration is an important indicator of sport endurance. Glycogen is the main energy source of high-intensity exercise, glycogen content can demonstrate the speed or degree that fatigue occurs. If the hepatic glycogen of test product group is significantly higher than control group, and the difference has statistical significance, it indicates that the test product can provide more energy for the body to achieve the purpose of anti-fatigue by increasing hepatic glycogen reserves. Serum urea nitrogen is a protein metabolite, after muscles sport energy homeostasis is destroyed, protein, amino acids and other nitrogen-containing compounds will be degraded, the take-off amino will form urea, the stronger the degradation of nitrogen-containing compounds is, the higher the blood urea content is, fatigue is more prone to occur.

Long-term sport will cause the body relatively hypoxia, glycolysis accelerate and further produce large amounts of lactic acid so that the lactic acid value in the muscle tissue will decrease, leading to fatigue, so the blood lactic acid level is also an important indicator of the body's aerobic metabolism ability and fatigue degree, with swimming duration as the index for detecting mouse fatigue, the length of swimming duration may reflect the degree of the animal exercise endurance, improved exercise tolerance is the most direct manifestation of enhanced antifatiguability. The drug having an anti-fatigue performance can make animals' swimming duration prolonged.

According to "Technical Standards for Testing & Assessment of Health Food (2003 edition)", the load swimming experiment, serum urea nitrogen assay, hepatic glycogen content assay and serum lactate dehydrogenase (LDH) assay experiment are carried out, wherein the result of load swimming experiment has statistical significance; any two experimental results of serum urea nitrogen assay, serum LDH assay and hepatic glycogen assay have statistical significance, the test sample is determined to have a physical fatigue-relieving function.

The index of each group in three dosage groups of the oral liquid of the present invention in four experiments, i.e., load swimming duration, hepatic glycogen experiment, LDH assay has significant difference, which shows a rather obvious dosage-effect relationship, and the effect of high dosage group is significant. The conclusion of present animal experiment study is that the test sample has physical fatigue-relieving function.

2.2.1 Animal Grouping

Each experiment was divided into four groups: blank control group (distilled water), high, medium and low-dosage experimental groups. 10 mice were randomly assigned to each group. The mice in each group were continuously intragastrically administrated for 30 d, no diet control during the experiment period. Body weight was weighed every 6 d, recorded, and the administration amount was adjusted according to body weight change.

2.2.2 Preparation of the Test Product

Equivalent dosage of mouse is equal to 10 folds of the human body recommended amount, 0.134 mL/per/day of the test product is the low dosage, 0.268 mL/per/day is the medium dosage, 0.402 mL/per/day is the high dosage. After a continuously intragastric administration of equal volume of the test product for 30 d, each index was measured.

2.2.3 Measurement Index

Except body weight change during administration period, the experiment measures 4 indices, which are respectively load swimming duration, serum urea nitrogen assay, serum LDH assay and hepatic glycogen assay.

2.2.4 Experimental Methods 2.2.4.1 Load Swimming Experiment

The mice in each group were continuously intragastrically administrated for 30 d, the blank control group was administrated with equal volume of solvent. 30 min after the last administration, the mouse with root of tail loaded with the iron wire 5% of body weight was placed in the swimming tank to swim, the depth of water being 30 cm±2 cm, water temperature being 25±1.0, the duration of mouse from the beginning of swimming to death was recorded, i.e., the load swimming duration of mouse, accurate to second.

2.2.4.2 Serum Urea Nitrogen Assay Experiment

The mice were continuously intragastrically administrated for 30 d, the blank control group was administrated with equal volume of solvent. 30 min after the last administration, mice swam for 90 min without load in the water at the temperature of 30±1, after rested for 60 min, blood was taken from the eye. Serum was obtained by centrifugation after clotting. The content of serum urea nitrogen was assayed by automatic blood biochemical analyzer.

2.2.4.3 Serum LDH Assay Experiment

The mice were continuously intragastrically administrated for 30 d, the control group was administrated with equal volume of solvent. 30 min after the last administration, after mice swam for 10 min without load in the water at the temperature of 30±1, blood was taken from the eye. Serum was obtained by centrifugation after clotting. The content of serum LDH was assayed by automatic blood biochemical analyzer.

2.2.4.4 Hepatic Glycogen Assay

The mice in each group were continuously intragastrically administrated for 30 d. 30 min after the last administration, the mouse was executed, liver were taken upon, rinsed with physiological saline, then dried with filter paper, 100 mg of liver were weighed accurately to prepare hepatic glycogen, the content of hepatic glycogen was measured.

2.2.5 Statistical Analysis

Data conversion and statistical analysis are performed using SPSS13.0 software. During the analysis, firstly, homogeneity of variance test is performed on the data, if there is homogeneity of variance, overall comparison is performed using ANOVA, if difference is found, pairwise comparisons are then performed by LSD method or Dunnett's method between the means of multiple dosage groups and control group. If there lacks heterogeneity of variance, then appropriate variable conversion is performed on the original data, statistics is performed on the converted data after satisfying the requirement of homogeneity of variance test, if the variable after conversion still can not satisfy the requirement of homogeneity of variance, changed to rank sum test to perform statistics, if difference is found when using overall comparison, pairwise comparisons are performed by the Tamhane's T2 test without requiring homogeneity of variance. As a result, groups are compared by mean and standard deviation ($X \pm S$).

2.2.6 Determination of Result

According to "Technical Standards for Testing & Assessment of Health Food (2003 edition)", the test sample is determined to have efficacy of alleviating physical fatigue according to the following standard.

Result of load swimming experiment has statistical significance;

any two experimental results of serum urea nitrogen assay, serum LDH assay and hepatic glycogen assay have statistical significance.

2.2.6.1 Load swimming experiment, results are as shown in the following Table 4: from the comparison of three dosage (high, medium, low) groups of the oral liquid of the present invention and blank group, the administration dosage and the mean of swimming duration of the animals of experiment group show a dosage-effect relationship. The load swimming survival duration of the mice in high dosage group increases significantly, has a statistical significance. From the experiment result of load, it is known from variance analysis (homogeneity of variance) that, F swimming duration=2.596, P swimming duration=0.036, <0.05, which demonstrates that the load swimming duration after administration of test product of each group of mice have obvious difference, thus shows that the intragastric administration of test product can cause obvious prolonging of animal swimming duration. It shows that the test sample has an effect of prolonging the load swimming duration of mice.

TABLE 4

The comparison of load swimming duration of mice of each group of mice

| Grouping | Sample number | Swimming duration ($X \pm S$) | P value in comparison with blank group |
|---|---|---|---|
| blank group | 10 | 392.60 ± 52.23 | |
| low dosage group | 10 | 432.40 ± 76.31 | 0.171 |

TABLE 4-continued

The comparison of load swimming duration of mice of each group of mice

| Grouping | Sample number | Swimming duration ($X \pm S$) | P value in comparison with blank group |
|---|---|---|---|
| medium dosage group | 10 | 439.70 ± 38.17 | 0.107 |
| high dosage group | 10 | 492.40 ± 50.93 | 0.001 |

2.2.6.2 serum urea nitrogen content experiment, results are as shown in the following Table 5: from the comparison of three dosage (high, medium, low) groups of the oral liquid of the present invention and blank group, the mean of urea nitrogen content level of each of two experiment groups (low dosage group, high dosage group) of mice is lower than the blank group, while the medium dosage group is not obviously different from the blank group. The urea nitrogen level of three subject substance groups does not show concentration-effect relationship. It is assumed that the effect of test product on mouse urea nitrogen has a rather appropriate ingestion amount range, and the designed administration dosage in the experiment protocol is not within the range. The reason might also be a rather short administration period, though the experiment group has a tendency of reducing urea nitrogen, the reduction of urea nitrogen level does not show an obvious dosage-effect relationship.

TABLE 5

The comparison of serum urea nitrogen content of each group of mice

| Grouping | Sample number | Urea nitrogen content ($X \pm S$) | Significant difference from blank group |
|---|---|---|---|
| blank group | 10 | 10.31 ± 0.82 | |
| low dosage group | 10 | 9.04 ± 2.03 | 0.079 |
| medium dosage group | 10 | 10.23 ± 1.18 | 0.994 |
| high dosage group | 10 | 9.24 ± 1.15 | 0.136 |

2.2.6.3 LDH activity experiment: from the comparison of three dosage (high, medium, low) groups of the oral liquid of the present invention and blank group, comparison of low dosage and blank group show no statistical significance, which demonstrate that low dosage does not have an obvious effect on improving LDH activity of mice. The difference of medium dosage group, high dosage group from blank group show a significant difference, which demonstrate that the medium dosage, high dosage have an obvious effect on improving LDH activity of mice, from low dosage to high dosage, with the increase of administration concentration, the increase of LDH also show an increasing tendency, show a concentration-effect correspondence.

TABLE 6 mouse LDH content

| Grouping | Sample number | LDH ($X \pm S$) | P value obtained after compared with blank group |
|---|---|---|---|
| blank group | 10 | 650.6 ± 139.4 | |
| low dosage group | 10 | 539.7 ± 187.6 | 0.228 |
| medium dosage group | 10 | 818.0 ± 165.3 | 0.071 |
| high dosage group | 10 | 880.8 ± 243.2 | 0.014 < 0.05 |

2.2.6.4 Hepatic glycogen experiment: the comparison of three dosage (high, medium, low) groups of the oral liquid of the present invention and blank group, the mean of hepatic glycogen content of each experiment group of mice is higher than the mean of hepatic glycogen content of the blank group of mice, the difference of hepatic glycogen content of the high dosage group of mice has statistical significance. This demonstrates that the test product can reduce the consumption of hepatic glycogen, improve the effect of hepatic glycogen content. From low dosage to high dosage, with the increase of administration concentration, hepatic glycogen content also shows an increasing tendency, and shows a concentration-response correspondence.

TABLE 7

The comparison of hepatic glycogen content of mice

| Grouping | Sample number | Hepatic glycogen (X ± S) | P value in comparison with blank group |
|---|---|---|---|
| blank group | 10 | 674.065 ± 194.399 | |
| low dosage group | 10 | 775.491 ± 243.308 | 0.352 |
| medium dosage group | 10 | 840.697 ± 214.472 | 0.129 |
| high dosage group | 10 | 1113.607 ± 226.085 | 0.000 < 0.05 |

To sum up, in condition of the present experiment lab, continuous orally intragastrically administrate with distilled water, and test sample respectively, each for 30 days, in four sub-experiments of the anti-fatigue experiment of the present health-care product, the index of each group in load swimming duration, hepatic glycogen experiment, LDH assay has a significant difference, showing a rather obvious dosage-effect relationship, and the effect of high dosage group is significant. The difference among each group of urea nitrogen experiment has no statistical significance. According to "Technical Standards for Testing & Assessment of Health Food (2003 edition)", the conclusion of present animal experiment study is that the test sample has a physical fatigue-relieving function.

Therefore, the health food of the present invention, the active ingredients of the health food are prepared with natural Chinese herbal medicine as the raw materials, the prepared health food has anoxia-tolerant and anti-fatigue functions at the same time.

Some specific examples are listed as above to illustrate the present invention, it should be noted that the aforesaid specific examples are merely for further illustrate the present invention, and should not be deemed as a limitation to the protection scope of the present invention. Some non-substantial modification and adjustment made by the other people according to the present invention still fall into the protection scope of the present invention.

What is claimed is:

1. A method for enhancing anoxia-tolerant and anti-fatigue functions in a human subject by administering a dietary supplement, wherein said dietary supplement comprises hot water extracts from active ingredients consisting of Arillus Longan, Fructus Jujubae, Radix Rehmanniae Preparata, Fructus Lycii, Semen Juglandis, Fructus Schisandrae Chinensis, Cortex Cinnamomi, and Cornu Cervi Pantotrichum.

2. The method according to claim 1, wherein said dietary supplement has a dosage form which is tablet, capsule, powder, granule, effervescent agent, drink, mixture or oral liquid.

3. The method according to claim 1, wherein the weight ratio of the active ingredients Arillus Longan:Fructus Jujubae:Radix Rehmanniae Preparata:Fructus Lycii:Semen Juglandis:Fructus Schisandrae Chinensis:Cortex Cinnamomi:Cornu Cervi Pantotrichum is 10-150:10-150:10-150:10-150:10-150:3-50:3-50:3-50.

4. The method according to claim 3, wherein said dietary supplement has a dosage form which is tablet, capsule, powder, granule, effervescent agent, drink, mixture or oral liquid.

5. The method according to claim 1, wherein the weight ration of the active ingredients Arillus Longan:Fructus Jujubae:Radix Rehmanniae Preparata:Fructus Lycii:Semen Juglandis:Fructus Schisandrae Chinensis:Cortex Cinnamomi:Cornu Cervi Pantotrichum is 20-90:20-90:20-90:20-90:15-90:5-20:3-20:3-20.

6. The method according to claim 5, wherein said dietary supplement has a dosage form which is tablet, capsule, powder, granule, effervescent agent, drink, mixture or oral liquid.

7. The method according to claim 5, wherein the weight ratio of the active ingredients Arillus Longan:Fructus Jujubae:Radix Rehmanniae Preparata:Fructus Lycii:Semen Juglandis:Fructus Schisandrae Chinensis:Cortex Cinnamomi:Cornu Cervi Pantotrichum is 25:25:20:20:15:8:5:5.

8. The method according to claim 7, wherein said dietary supplement has a dosage form which is tablet, capsule, powder, granule, effervescent agent, drink, mixture or oral liquid.

* * * * *

UNITED STATES PATENT AND TRADEMARK OFFICE
CERTIFICATE OF CORRECTION

PATENT NO. : 9,707,262 B2
APPLICATION NO. : 14/715619
DATED : July 18, 2017
INVENTOR(S) : Hongwei Zhao It is certified that error appears in the above-identified patent and that said Letters Patent is hereby corrected as shown below:

In the Claims

The term "ration" in Claim 5 should be corrected to "ratio".

Signed and Sealed this
Seventeenth Day of October, 2017

Joseph Matal
*Performing the Functions and Duties of the
Under Secretary of Commerce for Intellectual Property and
Director of the United States Patent and Trademark Office*